United States Patent
Murayama et al.

(10) Patent No.: US 7,365,379 B2
(45) Date of Patent: Apr. 29, 2008

(54) SOLID STATE IMAGING UNIT AND ENDOSCOPE

(75) Inventors: Jin Murayama, Miyagi (JP); Tatsuya Hagiwara, Miyagi (JP)

(73) Assignee: Fujifilm Corporation, Minato-ku, Tokyo (JP)

( * ) Notice: Subject to any disclaimer, the term of this patent is extended or adjusted under 35 U.S.C. 154(b) by 221 days.

(21) Appl. No.: 11/150,182

(22) Filed: Jun. 13, 2005

(65) Prior Publication Data

US 2005/0280055 A1 Dec. 22, 2005

(30) Foreign Application Priority Data

Jun. 22, 2004 (JP) ............................. 2004-183868

(51) Int. Cl.
*H01L 29/72* (2006.01)
(52) U.S. Cl. ............... 257/291; 257/292; 257/215; 257/440; 257/443
(58) Field of Classification Search ............. 257/291, 257/292, 215, 440, 443
See application file for complete search history.

(56) References Cited

U.S. PATENT DOCUMENTS 6,573,750 B2 * 6/2003 Mutoh et al. .................. 326/61

FOREIGN PATENT DOCUMENTS

| JP | 7-202152 | 8/1995 |
|----|----------|--------|
| JP | 2004-6834 | 1/2004 |

* cited by examiner

*Primary Examiner*—Edward Wojciechowicz
(74) *Attorney, Agent, or Firm*—McGinn IP Law Group, PLLC (57) ABSTRACT

A solid state image pickup device includes: a first area defined on a principal surface of a semiconductor substrate; a second area defined in an area adjacent to the first area along a first direction; and a third area defined in an area adjacent to the second area along the first direction, wherein the first area includes: a plurality of photoelectric conversion elements; and a plurality of vertical transfer channels formed adjacent to the plurality of photoelectric conversion elements; the second area includes: a horizontal transfer channel; and a floating diffusion region and a first stage drive FET of an amplifier; and the third area includes: a first state load FET, a second stage drive FET, a second stage load FET, a third stage drive FET and a third stage load FET, respectively of the amplifier. The solid state image pickup device can be made compact.

20 Claims, 6 Drawing Sheets

SOLID STATE IMAGING UNIT AND ENDOSCOPE

CROSS REFERENCE TO RELATED APPLICATION

This application is based on and claims priority of Japanese Patent Application No. 2004-183868 filed on Jun. 22, 2004, the entire contents of which are incorporated herein by reference.

BACKGROUND OF THE INVENTION

A) Field of the Invention

The present invention relates to a solid state imaging unit and an endoscope using the solid state imaging unit.

B) Description of the Related Art

Figure 5A:
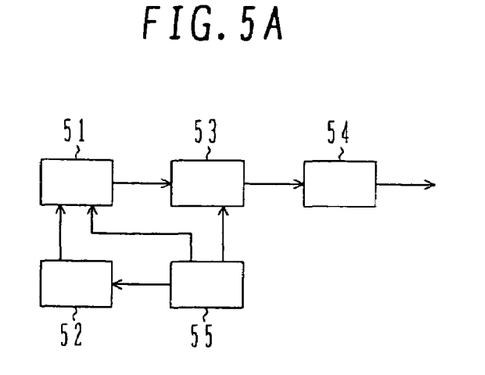
FIG. 5A is a block diagram showing a main portion of a solid image pickup device assembling a solid state imaging unit.
Figure 5B:
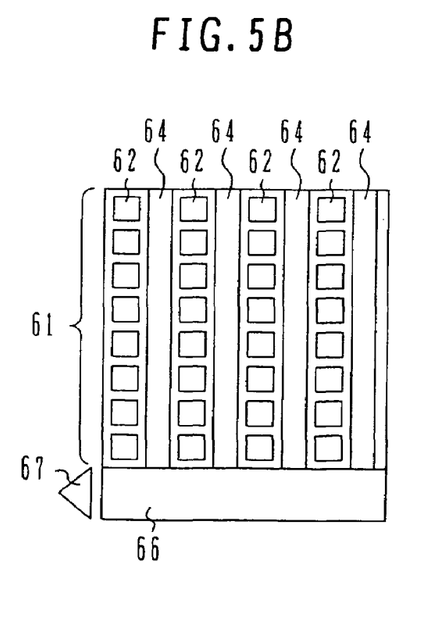
FIGS. 5B and 5C are schematic plan views showing the structure of a solid state imaging unit.
Figure 5C:
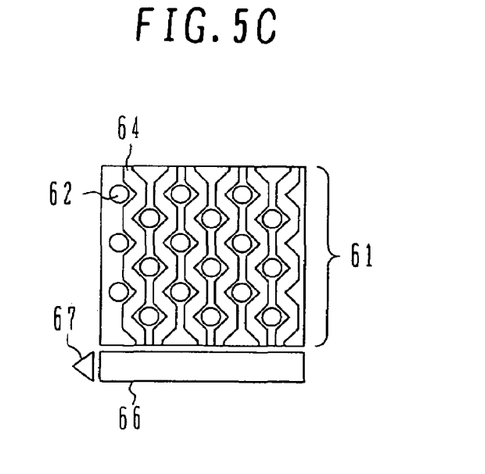
Figure 5D:
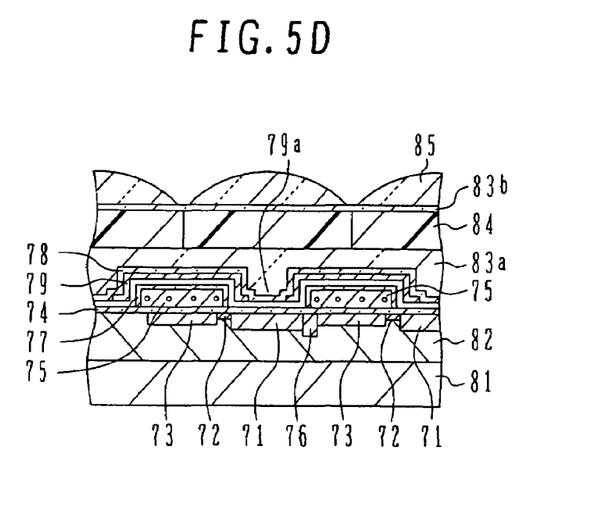
FIG. 5D is a cross sectional view showing a portion of a light reception portion of a solid state imaging unit.

FIG. 5A is a block diagram showing a main portion of a solid image pickup device assembling a solid state imaging unit, and FIGS. 5B and 5C are schematic plan views showing the structure of a solid state imaging unit. FIG. 5D is a cross sectional view briefly showing a portion of a light reception portion of a solid state imaging unit.

Referring to FIG. 5A, the structure of a solid state image pickup device will be described. A solid state imaging unit 51 generates signal charges corresponding to an amount of light incident upon each pixel and supplies an image signal corresponding to the generated signal charges. A drive signal generator 52 generates drive signals (transfer voltage, etc.) for driving the solid state imaging unit 51 and supplies them to the solid state imaging unit 51. An analog front end (AFE) 53 performs correlation double sampling of an output signal of the solid state imaging unit 51, amplifies the sampled signal at an externally set gain, performs analog-digital conversion and outputs a digital signal. A digital signal processor (DSP) 54 processes an image signal supplied from the analog front end 53, such as recognition process, data compression and network control, and outputs the processed image data. A timing generator (TG) 55 generates timing signals for the solid state imaging unit 51, drive signal generator 52 and analog front end 53, to control the operations thereof.

Solid state imaging units are mainly divided into CCD types and MOS types. In the CCD type, charges generated in a pixel is transferred by charge coupled devices (CCD). In the MOS type, charges generated in a pixel are amplified by a MOS transistor and output. Although not limitative, the following description will be made by using a CCD type as an example.

The drive signal generator 52 includes, for example, a V driver for generating a vertical CCD drive signal. Signals supplied from the drive signal generator 52 to the solid state imaging unit 51 are a horizontal CCD drive signal, a vertical CCD drive signal, an output amplifier drive signal and a substrate bias signal.

As shown in FIG. 5B, the solid state imaging unit is constituted of: a plurality of photosensitive units 62 disposed, for example, in a matrix shape; a plurality of vertical CCD units 64, a horizontal CCD unit 66 electrically connected to the vertical CCD units 64; and an amplifier circuit unit 67, connected to an output terminal of the horizontal CCD unit 66, for amplifying an output charge signal from the horizontal CCD unit 66. A light reception portion (pixel arrangement unit) 61 is constituted of the photosensitive units 62 and vertical CCD units 64.

The photosensitive unit 62 is constituted of a photosensitive element, e.g., a photoelectric conversion element (photodiode) and a read out gate. The photoelectric conversion element generates signal charges corresponding to an incidence light amount and accumulates them. The accumulated signal charges are read via the read out gate to the vertical CCD unit 64 and transferred in the vertical CCD unit (vertical transfer channel) 64 as a whole toward the horizontal CCD unit 66 (in a vertical direction). Signal charges transferred to the bottom end of the vertical CCD unit 64 are transferred in the horizontal CCD unit (horizontal transfer channel) 66 as a whole in a direction crossing a vertical direction, e.g., in a horizontal direction (a direction perpendicular to a vertical direction), and thereafter converted into a voltage signal. The voltage signal is applied to an amplifier 67, amplified and output.

The photosensitive units 62 are disposed in a square matrix layout at a constant pitch in the row and column directions as shown in FIG. 5B, or disposed in a honeycomb layout in the row and column directions by shifting every second units, for example, by a half pitch.

FIG. 5C is a schematic plan view of a solid state imaging unit having the pixel interleaved layout. The pixel interleaved layout has photosensitive units 62 disposed in a first square matrix layout and photosensitive units 62 disposed in a second square matrix layout at positions between lattice points of the first square matrix layout. Vertical CCD units (vertical transfer channels) 64 are disposed in a zigzag way between photosensitive units 62. Also in this case, signal charges are transferred in the vertical transfer channel as a whole in a direction (vertical direction) toward the horizontal CCD unit 66. Although this layout is called a pixel interleaved layout, the photosensitive unit 62 of most pixel interleaved layouts is octangular.

As shown in FIG. 5D, formed in a p-type well 82 formed in a semiconductor substrate 81, e.g., an n-type silicon substrate, are a photoelectric conversion element 71 made of an n-type impurity doped region, a p-type read gate 72 disposed next to the photoelectric conversion element 71, and a vertical transfer channel 73 of made of an n-type region disposed next to the read gate 72. A vertical transfer electrode 75 is formed above the vertical transfer channel 73, with a gate insulating film 74 being interposed therebetween. A p-type channel stop region 76 is formed between adjacent photoelectric conversion elements 71.

The channel stop region 76 is used for electrically isolating the photoelectric conversion elements 71, vertical transfer channels 73 and the like. The gate insulating film 74 is a silicon oxide film formed on the surface of the semiconductor substrate 81, for example, by thermal oxidation. The vertical transfer electrode 75 is constituted of first and second vertical transfer electrodes made of, for example, polysilicon. The first and second vertical transfer electrodes may be made of amorphous silicon. An insulating silicon oxide film 77 is formed on the vertical transfer electrode 75, for example, by thermally oxidizing polysilicon. The vertical CCD unit 64 is constituted of the vertical transfer channel 73, upper gate insulating film 74 and vertical transfer electrode 75. The horizontal CCD unit 66 is constituted of a horizontal transfer channel, upper gate insulating film and horizontal transfer electrode.

A light shielding film 79 of, e.g., tungsten, is formed above the vertical transfer electrode 75, with the insulating silicon oxide film 77 being interposed therebetween. Openings 79a are formed through the light shielding film 79 at positions above the photoelectric conversion elements 71. A silicon nitride film 78 is formed on the light shielding film 79. The silicon nitride film 78 is not necessarily required.

Signal charges corresponding to an incidence light amount generated in the photoelectric conversion element 71 are read via the read out gate 72 into the vertical transfer channel 73 and transferred in the vertical transfer channel 73 in response to a drive signal (transfer voltage) applied to the vertical transfer electrodes 75. As described above, the light shielding film 79 has the openings 79a above the photoelectric conversion elements 71 and prevents light incident upon the light reception portion 61 from entering the region other than the photoelectric conversion elements 71.

A planarized layer 83a made of, e.g., borophosilicate glass (BPSG) is formed above the light shielding film 79. On this planarized surface, a color filter layer 84 is formed which is three primary colors: red (R), green (G) and blue (B). Another planarized layer 83b is formed on the color filter layer 84. On the planarized layer 83 having a planarized surface, micro lenses 85 are formed, for example, by melting and solidifying a photoresist pattern of micro lenses. Each micro lens 85 is a fine hemispherical convex lens disposed above each photoelectric conversion element 71. The micro lens 85 converges incidence light to the photoelectric conversion elements 71. Light converged by one micro lens 85 passes through the color filter layer 84 of one of the red (R), green (G) and blue (B) and becomes incident upon one photoelectric conversion element 71. Therefore, the photoelectric conversion elements include three types of photoelectric conversion elements: photoelectric conversion elements upon which light passed through the red (R) color filter layer 84 becomes incident; photoelectric conversion elements upon which light passed through the green (G) color filter layer 84 becomes incident; and photoelectric conversion elements upon which light passed through the blue (B) color filter layer 84 becomes incident.

In the specification and claims, "above" the photoelectric conversion element or the semiconductor substrate on which the photoelectric conversion elements are formed, intended to mean "at a higher position" in the above-described structure of the solid state imaging unit.

Figure 6:
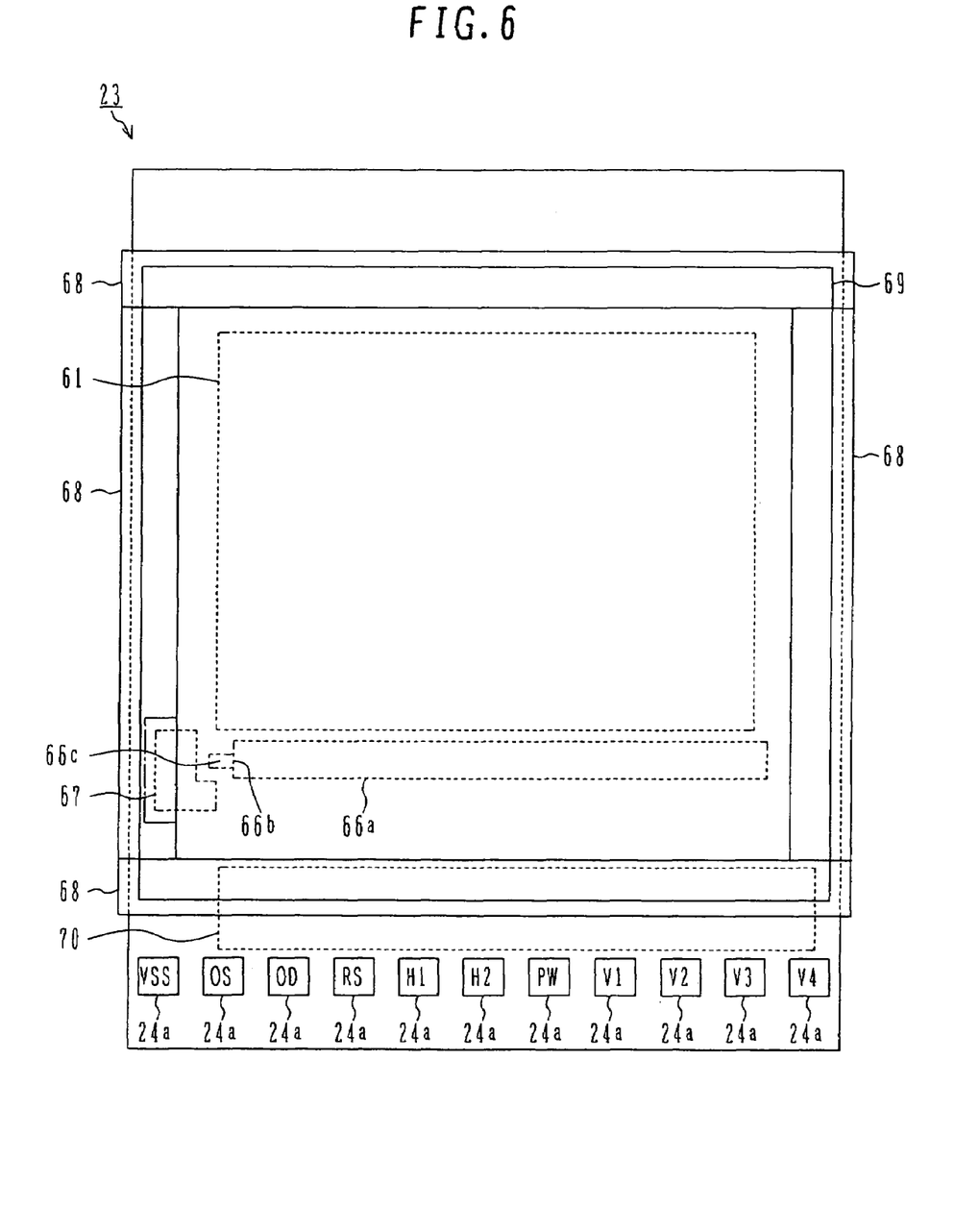
FIG. 6 is a schematic plan view of a semiconductor chip 23 formed with the solid state imaging unit shown in FIG. 5B or 5C.

FIG. 6 is a schematic plan view of a semiconductor chip 23 formed with the solid state imaging unit shown in FIG. 5B or 5C. The semiconductor chip 23 includes, in addition to the solid state imaging unit shown in FIG. 5B or 5C, a protective circuit 70, a spacer (a support member) 68, a protective glass (protective member) 69 and a plurality of pads 24a. A horizontal transfer channel 66a, a horizontal transfer channel output port 66b and a floating diffusion region 66c shown in FIG. 6 are elements constituting the horizontal CCD unit 66 shown in FIG. 5B or 5C.

The protective circuit 70 is used for mitigating unfavorable events in the solid state imaging unit. The spacer 68 is formed on the principal surface of a semiconductor substrate formed with photoelectric conversion elements, surrounding as viewed in plan the solid state imaging unit. A thickness of the spacer 68 is, e.g., 100 μm. The spacer 68 is adhered to the surface of the semiconductor substrate, for example, with adhesive. On the spacer 68, the protective glass 69 of transparent material is placed which has a thickness of, e.g., 250 μm.

The protective glass 69 protects the solid state imaging unit from moisture and mechanical factors which might damage the solid state imaging unit. The semiconductor chip 23 is manufactured by forming a number of solid state imaging units on a silicon wafer and dicing each solid state imaging unit. The protective glass 69 can prevent dust, which is formed during the manufacture processes, mainly the dicing process and subsequent processes, from attaching the light reception portion 61. One of mount processes is a sealing process of sealing the solid state imaging unit by the spacer 68 and protective glass 69.

The pads 24a are external interconnection terminals for electrical connection between the semiconductor chip 23 and a wiring board formed with a driver circuit and the like and wirings. This electrical connection will be later described.

Signal charges generated and accumulated in the light reception portion (pixel arrangement unit) 61 are transferred to the horizontal transfer channel 66a in the manner described earlier, and transferred in the horizontal transfer channel 66a toward the horizontal transfer channel output port 66b and arrive at the floating diffusion region 66c. The signal charges are converted into a voltage at the floating diffusion region 66c, and the converted voltage is sent to an amplifier 67 whereat the voltage signal is amplified and output to an external.

The size of each pixel of a solid state imaging unit including CCDs is reduced as a number of pixels are used. This size reduction makes smaller the size of an effective light reception portion of pixels. On-chip micro lenses are used widely in order to improve an effective aperture ratio of each pixel.

A solid state image pickup device mounting compact micro lenses is disclosed (for example, refer to Japanese Patent Laid-open Publication No. HEI-7-202152), in which a sealing member made of transparent material and integrally forming a frame on a bottom border area thereof is disposed only on a light reception portion of a solid state imaging unit chip with the micro lenses, and the solid state imaging unit and the sealing member are hermetically sealed with a space of 5 μm or broader being formed between the surface of the micro lenses and the bottom surface of the sealing member.

A method is disclosed for manufacturing a solid state image pickup device capable of being manufactured with ease and at high reliability while the needs for compactness are met (for example, refer to Japanese Patent Laid-open Publication No. 2004-6834).

In the solid state imaging unit whose protective glass 69 is disposed above the semiconductor chip 23 by using the spacer 68, it is desired to adhere the spacer 68 to the semiconductor chip 23 near at the light reception portion 61 of the solid state imaging unit, in order to make compact the semiconductor chip 23 and hence the solid state image pickup device.

As described above, when the spacer 68 is mounted on the semiconductor chip 23, adhesive is used. In this case, the adhesive may protrude to the inner space of the spacer 68.

The semiconductor chip 23 formed with the solid state imaging unit has unfavorable areas if the spacer 68 is mounted and adhesive is attached in these areas. The unfavorable areas if adhesive is attached in these areas, are the upper areas of the horizontal transfer channel 66a, floating diffusion region 66c and amplifier 67, among other areas.

One of the reasons that attachment of adhesion is not preferable, is a change in capacitive components to be caused by the attachment of adhesion and hence a change in electronical characteristics. For example, if adhesion is attached to the floating diffusion region 66c having an electronical capacitance of 10 to 100 fF and the electrical capacitance of only several fF changes, the electrical characteristics are influenced considerably.

The second reason that attachment of adhesion is not preferable, is that electric charges may be mixed in an adhesive layer. Adhesive contains often organic dielectric and charges with polarization may be mixed in the dielectric.

For example, the floating diffusion region 66c performs a charge-voltage conversion for transferred signal charges so that it is sensitive to charges as well as capacitive components and prone to a change in the characteristics by charges. It is therefore preferable to avoid attachment of adhesive.

It is therefore preferable to mount the semiconductor chip 23 by setting the spacer 68 away from the upper areas of the horizontal transfer channel 66a, floating diffusion region 66c and amplifier 67.

Some width of the spacer 68 is required in order to adhere securely the spacer 68 to the semiconductor chip 23. Although it is possible to partially narrow the width of the spacer 68, this is not preferable because an adhesion force in the narrow area becomes weak and the sealing performance in this narrow area may be degraded.

Reverting to FIG. 6, as the horizontal transfer channel 66a, floating diffusion region 66c and amplifier 67 are disposed in the layout shown, the amplifier 67 positions lower left of the light reception portion 61 and along the left side of the semiconductor chip 23. In order to make compact the semiconductor chip 23, the spacer 68 is placed traversing the upper area of the amplifier 67. However, since it is not preferable to adhere the spacer 68 to the semiconductor chip 23 in the upper area (the surface of the semiconductor chip 23) of the amplifier 67, the spacer 68 partially removing a portion which contacts this upper area is adhered to the surface of the semiconductor chip 23. In FIG. 6, the removed portion is indicated by a one-dot chain line. It is necessary for the removed portion to have a remaining width necessary for secure adhesion.

With this arrangement that the spacer 68 with the removed portion in contact with the upper area of the amplifier 67 is adhered and the protective glass 69 is placed on the spacer, it has been found unsatisfactory, however, in that the adhesion between the narrowed area of the spacer 68 and the semiconductor chip 23 is not good and a sufficient sealing performance may become difficult to obtain.

Since the spacer 68 with the four side is integrally molded, the sealing performance is not degraded by the reason of the structure of the spacer 68 itself. Even if the spacer is not integrally molded, the sealing performance can be retained by using adhesive or the like.

SUMMARY OF THE INVENTION

An object of this invention is to provide a compact solid state image pickup device.

Another object of this invention is to provide a compact endoscope.

According to one aspect of the present invention, there is provided a solid state image pickup device comprising: a first area defined on a principal surface of a semiconductor substrate; a second area defined in an area adjacent to the first area along a first direction; and a third area defined in an area adjacent to the second area along the first direction, wherein the first area includes: a plurality of photoelectric conversion elements for accumulating signal charges corresponding to an incidence light amount; and a plurality of vertical transfer channels formed adjacent to the plurality of photoelectric conversion elements, the plurality of vertical transfer channels transferring the signal charges read from the plurality of photoelectric conversion elements, as a whole along the first direction; the second area includes: a horizontal transfer channel for transferring the signal charges transferred from the vertical transfer channels, as a whole along a second direction crossing the first direction; and a floating diffusion region and a first stage drive FET of an amplifier, formed in an area protruded from an output port of the horizontal transfer channel along the second direction; and the third area includes: a first state load FET, a second stage drive FET, a second stage load FET, a third stage drive FET and a third stage load FET, respectively of the amplifier.

This solid state image pickup device is a compact solid state image pickup device, particularly compact along the second direction. The solid state image pickup device can be made compact without degrading its performance, even if a support member (spacer) is disposed surrounding the peripheral area of the solid state image pickup device and a transparent member (protective glass) is placed on the support member.

According to another aspect of the present invention, there is provided an endoscope comprising: a light source for emitting light; a solid state image pickup device comprising: a first area defined on a principal surface of a semiconductor substrate; a second area defined in an area adjacent to the first area along a first direction; and a third area defined in an area adjacent to the second area along the first direction, wherein the first area includes: a plurality of photoelectric conversion elements for accumulating signal charges corresponding to an incidence light amount; and a plurality of vertical transfer channels formed adjacent to the plurality of photoelectric conversion elements, the plurality of vertical transfer channels transferring the signal charges read from the plurality of photoelectric conversion elements, as a whole along the first direction; the second area includes: a horizontal transfer channel for transferring the signal charges transferred from the vertical transfer channels, as a whole along a second direction crossing the first direction; and a floating diffusion region and a first stage drive FET of an amplifier, formed in an area protruded from an output port of the horizontal transfer channel along the second direction; and the third area includes: a first state load FET, a second stage drive FET, a second stage load FET, a third stage drive FET and a third stage load FET, respectively of the amplifier; and a transmission tube accommodating the light source and the solid state image pickup device.

This endoscope realizes compactness. For example, the endoscope can be entered from a nose of a patient into the interior of the body so that speech is possible while the diagnosis is performed.

According to the present invention, it is possible to provide a compact solid state image pickup device.

According to the present invention, it is possible to provide a compact endoscope.

DESCRIPTION OF THE PREFERRED EMBODIMENTS

Figure 1A:
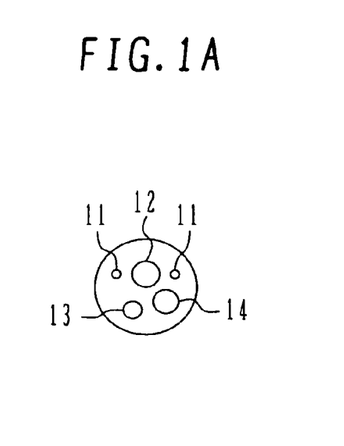
FIG. 1A is a schematic plan view showing the outline of a tip portion of an optical magnification electronic scope (endoscope) for observing precisely an upper digestive tract.
Figure 1B:
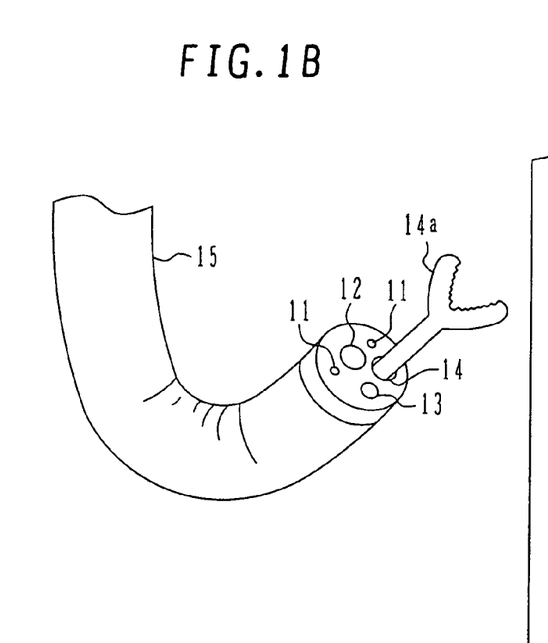
FIG. 1B is a perspective view showing the tip portion of the scope and a tube connected to the tip portion.
Figure 1C:
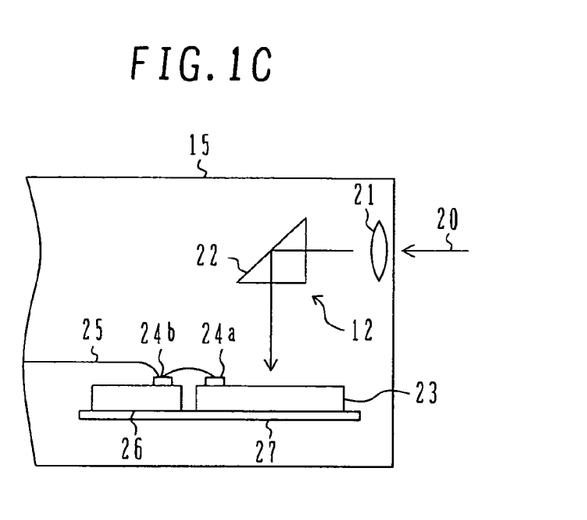
FIGS. 1C and 1D are schematic diagrams showing an observation optical system of the scope.
Figure 1D:
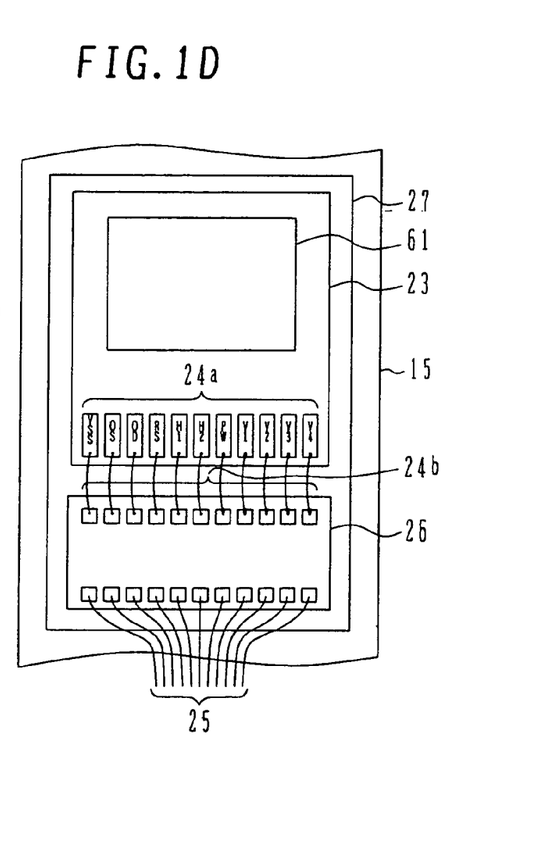

FIG. 1A is a schematic plan view showing the outline of a tip portion of an optical magnification electronic scope (endoscope) for observing precisely an upper digestive tract, FIG. 1B is a perspective view showing the tip portion of the scope and a tube connected to the tip portion, and FIGS. 1C and 1D are schematic diagrams showing an observation optical system of the scope.

Referring to FIG. 1A, the tip portion of an optical magnification electronic scope for observing precisely an upper digestive tract, is of generally the circular shape having a diameter of, e.g., 6.0 mm. This tip portion is constituted of a light source 11 with two light output openings, an observation optical system 12, a nozzle 13 and a forceps opening 14. The light source 11 includes a light emission source, a light guide (fiber) and light output openings. The electronic scope is used, for example, as a photogastroscope.

The light source 11 emits white light with light in the infrared range being cut, through the two light output openings and illuminates, e.g., the inner wall of a human gaster. The observation optical system 12 includes a solid state imaging unit similar to the solid state imaging unit described with reference to FIGS. 5B to 5D. The observation optical system 12 receives mainly light emitted from the light source 11 and reflected from the inner wall of the gaster, and forms an image which is sent to an observer. The observation optical system 12 will be later described in detail. The nozzle 13 jets out gas or liquid such as washing liquid and dye liquid for facilitating observation of a diseased part. A pair of forceps protrudes through the forceps opening 14 which has a diameter of, e.g., 2.8 mm.

Referring to FIG. 1B, the pair of forceps 14*a* is moved in and out through the forceps opening 14. The pair of forceps 14*a* has a tip portion which can perform an open/close operation like blades of a pair of scissors, and can hold a target member. By operating the pair of forceps 14*a*, it becomes possible to observe minutely a diseased part, pick up cells of the diseased part or cut the diseased part.

The light source 11, observation optical system 12, nozzle 13 and forceps 14*a* are accommodated in a tube 15, e.g., near the end portion thereof. For example, the tube 15 is guided into the interior of a body from a nose to make the end portion reach a position near a diseased part. As the tube is guided from not a mouth but a nose, diagnosis is possible while making speech with the patient. The scope guided from a nose has a smaller diameter than that of a scope guided from a mouth.

The tube 15 near the end portion is made flexible so that the observation optical system 12 and the like can be positioned nearer to the diseased part and the operability of the scope can be improved. A full length of the tube 15 is, e.g., 1400 mm. A manipulation apparatus is coupled to the end of the tube 15 opposite to the side where the observation optical system 12 and the like are disposed. The manipulation apparatus can operate the light source 11, observation optical system 12, nozzle 13 and forceps 14*a*. Image data from the observation optical system 12 is transmitted via the inside of the tube 15. The tube 15 is a mechanical and electrical transmission tube.

With reference to FIG. 1C, description will be made on the observation optical system 12. The observation optical system 12 is constituted of an objective lens 21, a prism 22, a semiconductor chip 23 and a wiring board 26. Light 20 emitted from the light source 11 and reflected from, e.g., the inner wall of a gaster, becomes incident upon the objective lens 21, is bent generally a right angle by the prism 22 which is an optical path changing device mounted above the solid state imaging unit, and becomes incident upon the semiconductor chip 23.

The semiconductor chip 23 has a solid state imaging unit such as that described with reference to FIGS. 5B to 5D, and pads 24*a*. These pads 24*a* of the semiconductor chip 23 are wire-bonded to pads 24*b* of the wiring board 26 on which a driver circuit and the like and wirings are formed. Lead wires 25 are connected to the pads 24*b* on the wiring board 26. The lead wires 25 extend in the tube 15 along its extension direction. The semiconductor chip 23 will be later described in detail.

Referring to FIG. 1D, light 20 becomes incident upon the objective lens 21, changes its propagation direction at the prism 22 and becomes incident upon the photoelectric conversion elements in the light reception portion 61 of the solid state imaging unit in the semiconductor chip 23 to generate and accumulate signal charges. The signal charges are transferred in the solid state imaging unit, processed in the manner described with reference to FIG. 5A, and output as image data. The image data is sent to an external via the lead wires 25.

Figure 2:
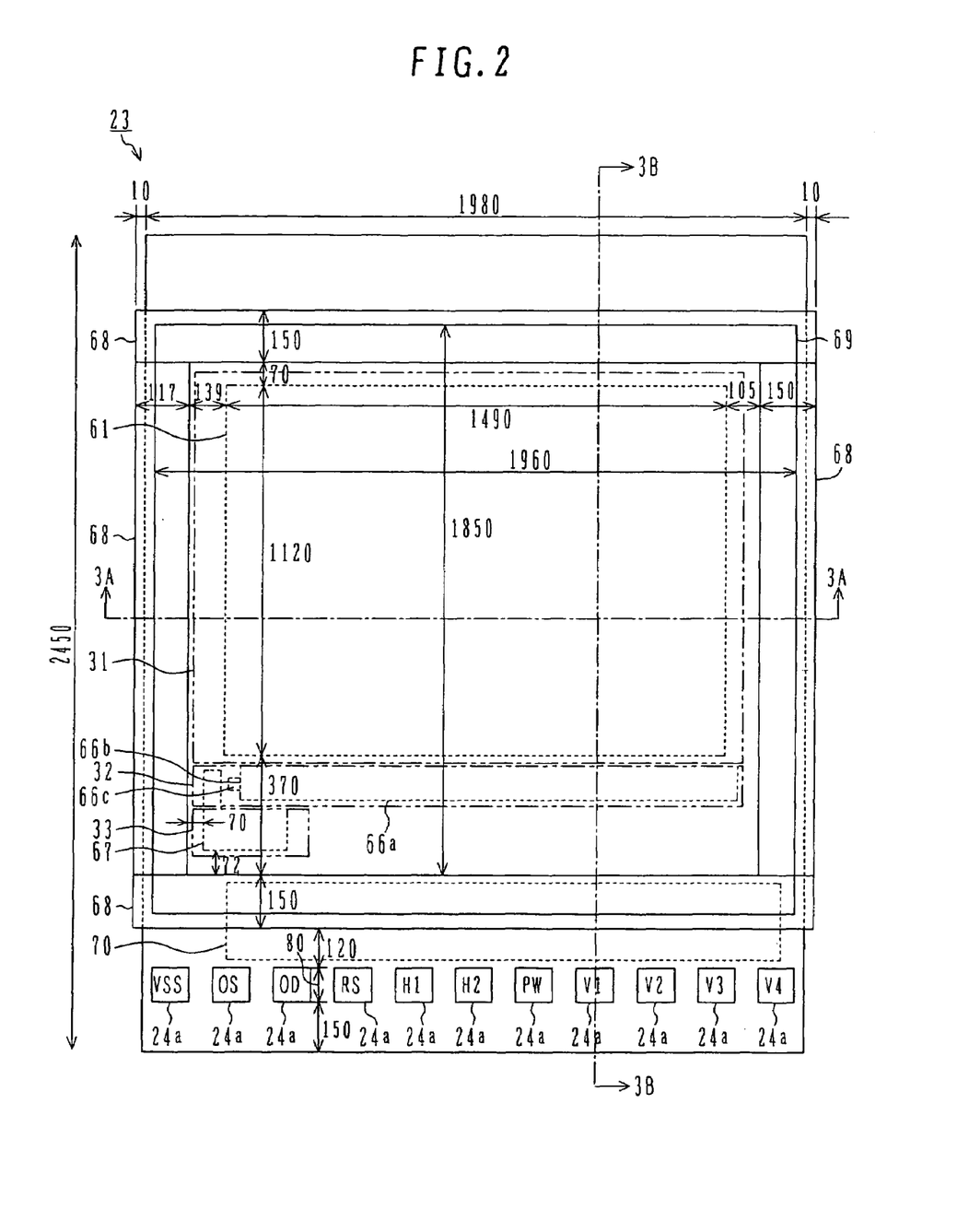
FIG. 2 is a schematic plan view of a fabricated semiconductor chip 23 used for the optical magnification electronic scope for observing precisely an upper digestive tract, shown in FIGS. 1A to 1D.

FIG. 2 is a schematic plan view of a fabricated semiconductor chip 23 used for the optical magnification electronic scope (endoscope) for observing precisely an upper digestive tract, shown in FIGS. 1A to 1D. FIG. 2 corresponds to FIG. 6 showing the related art.

As compared with the semiconductor chip 23 shown in FIG. 6, the characteristics of this embodiment reside in a different layout of an amplifier 67 of the semiconductor chip 23. This point will be later detailed. A spacer 68 can be mounted by positioning it away from the upper areas of a horizontal transfer channel 66*a*, a floating diffusion region 66*c* and an amplifier 67. It is therefore possible to prevent the electronical characteristics of each constituent element from being degraded by adhesion. Further, it is not necessary to form a partially narrowed portion of the spacer 68 so that adhesion and sealing will not be degraded. Furthermore, since the semiconductor chip 23 can be made more compact than that shown in FIG. 6, the scope using this semiconductor chip can be made compact.

The solid state imaging unit formed on the principal surface of the semiconductor chip 23 is formed in a first area 31 of, e.g., a rectangular shape, in a second area 32 of, e.g., a rectangular shape disposed under the first area (downward the vertical transfer direction), and in a third area 33 of, e.g., a rectangular shape disposed under the second area 32 (downward the vertical transfer direction).

The first area 31 includes photoelectric conversion elements 71 and vertical transfer channels 73.

Figure 4:
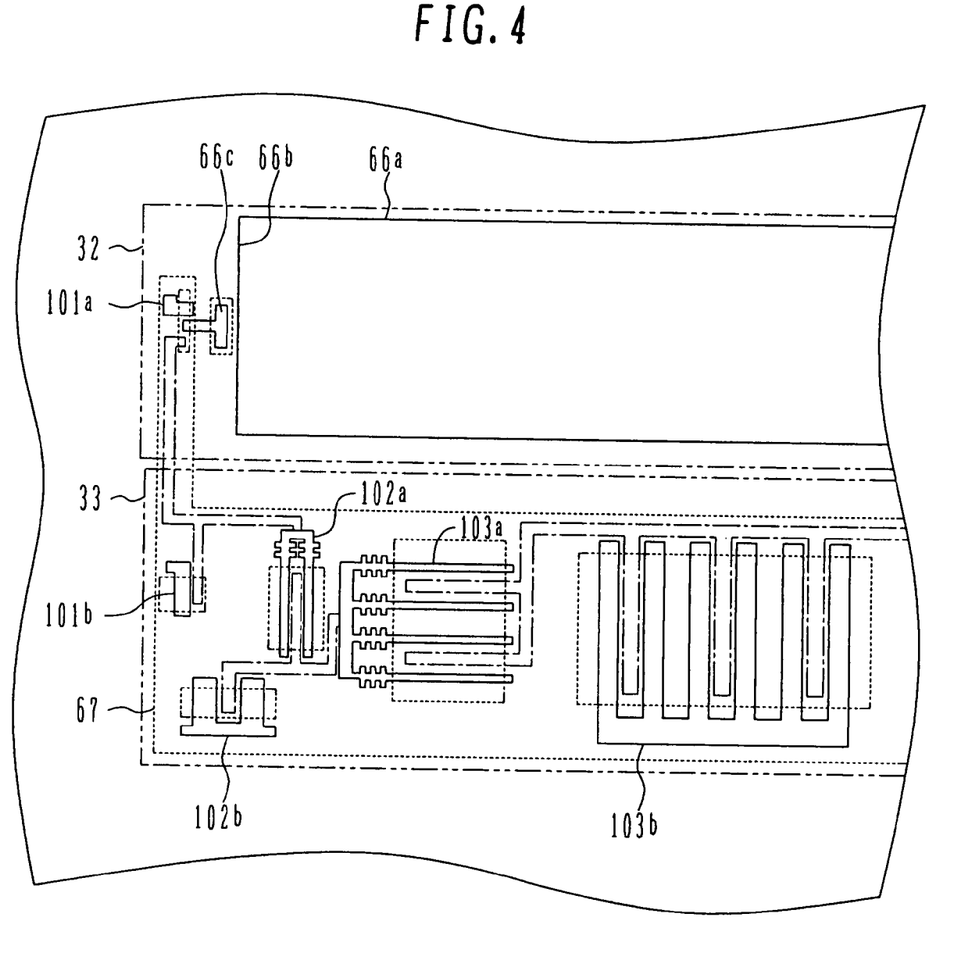
FIG. 4 is a schematic plan view showing the layout of a horizontal transfer channel 66a, a horizontal transfer channel output port 66*b*, a floating diffusion region 66*c* and an amplifier 67, respectively of the semiconductor chip 23.

Reference is made also to FIG. 4. The second area 32 includes the horizontal transfer channel 66*a*, floating gate diffusion region 66*c* and a first stage drive field effect transistor (FET) 101*a* of the amplifier 67.

The third area 33 includes a first stage load FET 101b, a second stage drive FET 102a, a second stage load FET 102b, a third stage drive FET 103a, and a third state load FET 103b, respectively of the amplifier 67.

These layouts will be later detailed with reference to FIG. 4.

The layout size of each area of the semiconductor chip 23 will be described. It is assumed that the semiconductor chip 23 is of a rectangular shape having a vertical length of 2450 µm (along the up/down direction in FIG. 2) and a horizontal length of 2000 µm (along a right/left direction in FIG. 2).

The light reception portion 61 is defined in a rectangular area having a vertical length of 1120 µm and a horizontal length of 1490 µm, and a pair of parallel sides of the rectangular area is parallel to a pair of parallel sides of the semiconductor chip 23.

A portion of the spacer 68 having a vertical length of 1560 µm and a horizontal length of 117 µm is mounted along the left side of the semiconductor chip 23 and a portion of the spacer 68 having a vertical length of 1560 µm and a horizontal length of 150 µm is mounted along the right side. A distance is 139 µm from the left side of the light reception area 61 to the spacer 68 at the left side of the semiconductor chip 23. A distance is 105 µm from the right side of the light reception area 61 to the spacer 68 at the right side of the semiconductor chip 23.

A portion of the spacer 68 having a vertical length of 150 µm and a horizontal length of 2000 µm is disposed on the upper side of the semiconductor chip 23, extending between the right and left sides of the semiconductor chip 23. A portion of the spacer 68 having a vertical length of 150 µm and a horizontal length of 2000 µm is disposed at the lower side of the semiconductor chip 23. A distance is 70 µm from the upper side of the light reception portion 61 to the spacer at the upper side of the semiconductor chip 23. A distance is 370 µm from the lower side of the light reception portion 61 to the spacer 68 at the lower side of the semiconductor chip 23. The four portions of the spacer 68 each have a rectangular shape as viewed in plan, and are formed on the principal surface on the semiconductor chip 23 with the light reception portion 61, surrounding the peripheral area of the solid state imaging unit.

The protective glass 69 placed on the spacer 68 has a vertical length of 1850 µm and a horizontal length of 1960 µm.

The pads 24a are disposed in line parallel to the lower side of the semiconductor chip 23. The pad 24a has a vertical length of 80 µm, a distance to the lower side spacer 68 is 120 µm and a distance to the lower side of the semiconductor chip 23 is 150 µm.

A distance is 70 µm as viewed in plan between the amplifier 67 and the left side spacer 68, and a distance is 72 µm as viewed in plan between the amplifier 67 and the lower side spacer.

In the optical magnification electronic scope (endoscope) for observing precisely an upper digestive tract shown in FIGS. 1A to 1D, the semiconductor chip 23 is disposed so that the upper side is near the objective lens 21. Therefore, light incident upon the objective lens 21 before reflected by the prism 22 propagates along a direction from the light reception portion 61 to the horizontal transfer channel 66a and to the pads 24a (along a direction that signal charges are transferred as the whole in the vertical transfer channels 73 in the light reception portion 61).

Figure 3A:
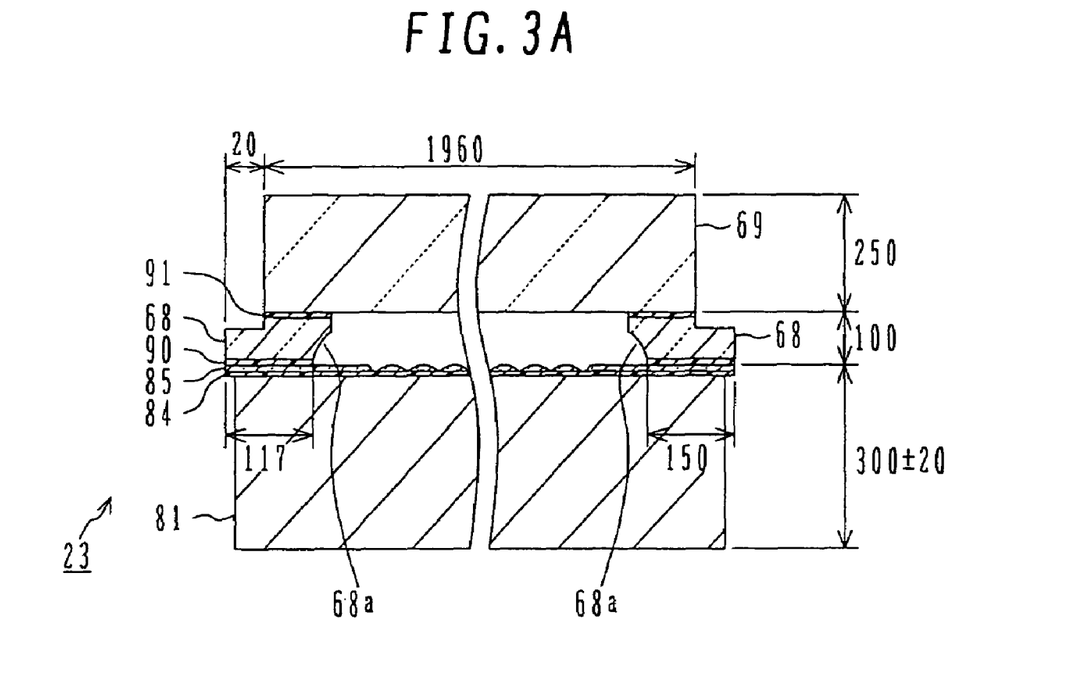
FIG. 3A is a partially broken cross sectional view taken along line 3A-3A shown in FIG. 2.
Figure 3B:
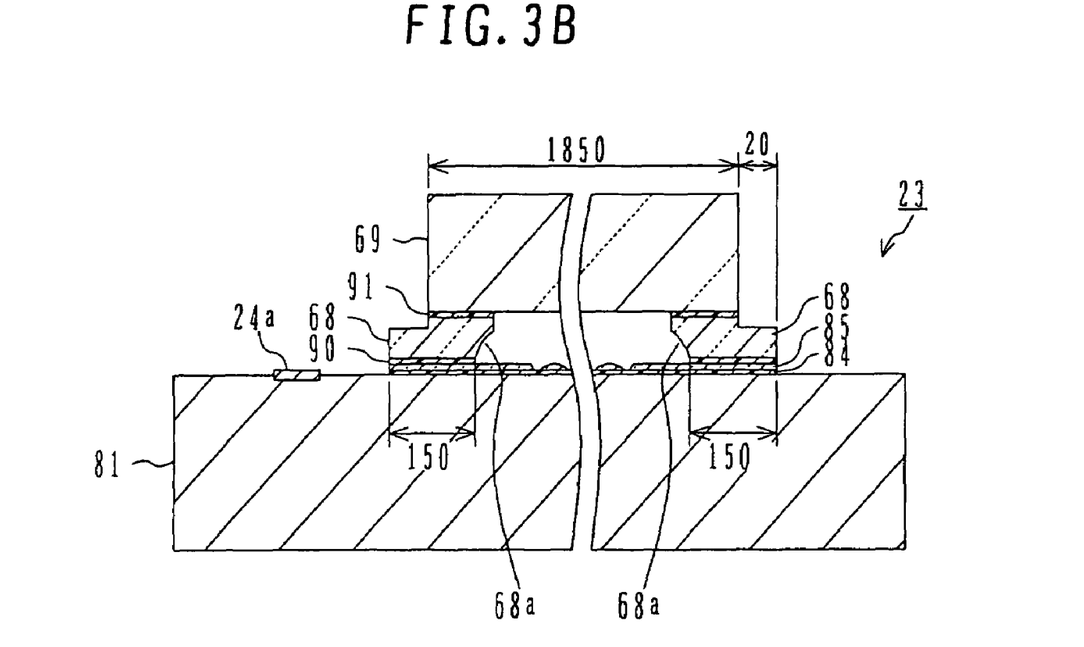
FIG. 3B is a partially broken cross sectional view taken along line 3B-3B shown in FIG. 2.

FIG. 3A is a partially broken cross sectional view taken along line 3A-3A shown in FIG. 2, and FIG. 3B is a partially broken cross sectional view taken along line 3B-3B shown in FIG. 2.

Referring to FIG. 3A, a height (thickness) between the bottom of the semiconductor substrate 81 to the micro lens 85 is, e.g., 300 µm, with an error range of ±20 µm.

On the micro lenses 85, the spacer 68 is adhered with adhesive 90. Uniform recesses 68a are formed in the spacer 68 on the side where the spacer contacts the surface of the semiconductor chip 23. The recesses 68a are formed on the inner side walls of the spacer 68 (on the side of the light reception portion 61).

A width of an area where the surface of the semiconductor chip 23 is adhered to the spacer 68 is 117 µm for the portion of the spacer 68 along the left side of the semiconductor chip 23 shown in FIG. 2 (the left side spacer 68 in FIG. 3A), and 150 µm for the portion of the spacer 68 along the right side of the semiconductor chip 23 (the right side spacer 68 in FIG. 3A).

The protective glass 69 is adhered to the spacer 68 with adhesive 91. The spacer 68 including the upper and lower adhesive 90 and 91 has a thickness of 100 µm. A thickness of the protective glass 69 is 250 µm. Both thicknesses may be changed by maintaining the total thickness, for example, at 350 µm.

Referring to FIG. 3B, in addition to the portions of the spacer 68 along the right and left sides of the semiconductor chip 23 shown in FIG. 2, also the portions of the spacer 68 along the upper and lower sides are formed with uniform recesses 68a on the side where the spacer contacts the surface of the semiconductor chip 23. The recesses 68a are formed on the inner side walls of the spacer 68 (on the side of the light reception portion 61).

A width of an area where the surface of the semiconductor chip 23 is adhered to the spacer 68 is 150 µm for the portion of the spacer 68 along the upper side of the semiconductor chip 23 shown in FIG. 2 (the right side spacer 68 in FIG. 3B), and 150 µm for the portion of the spacer 68 along the lower side of the semiconductor chip 23 (the left side spacer 68 in FIG. 3B).

The spacer 68 shown in FIGS. 3A and 3B has not a partially narrowed structure but a straight structure (the equal width adhesion area along the longitudinal direction of the spacer 68). A width of the adhesion area of the spacer 68 may preferably be 100 µm or wider in order to retain good adhesion and sufficient sealing performance.

FIG. 4 is a schematic plan view showing the layout of the horizontal transfer channel 66a, horizontal transfer channel output port 66b, floating diffusion region 66c and amplifier 67, respectively of the semiconductor chip 23. FIG. 4 shows the more detailed layout than that shown in FIG. 2.

The amplifier 67 is constituted of the first stage drive FET 101a, first stage load FET 101b, second stage drive FET 102a, second stage load FET 102b, third stage drive FET 103a and third stage load FET 103b.

In the second area 32, the floating diffusion region 66c and the first stage drive FET 101a of the amplifier 67 are disposed to the left of the horizontal transfer channel output port 66b (on the left side of the semiconductor chip 23 shown in FIG. 2, along the horizontal transfer direction as viewed from the horizontal transfer channel output port 66b).

The third area 33 is defined under the horizontal transfer channel 66a, floating diffusion region 66c and first stage drive FET 101a (second area 32). Disposed in the third area 33 are the first stage load FET 101b, second stage drive FET 102a, second stage load FET 102b, third stage drive FET 103a and third stage load FET 103b among the constituent elements of the amplifier 67. If a four stage drive or load FET or subsequent stage drive or load FETs exist, these FETs are also disposed in the third area 33.

With this layout, for example, the projection of the amplifier 67 to the left side can be reduced without lowering the sensitivity of the first stage drive FET 101a. The area to the left of the amplifier 67, in the unfavorable areas if adhesive is attached in these areas or the spacer 68 is mounted in theses areas (the upper areas of the horizontal transfer channel 66a, floating diffusion region 66c and amplifier 67) can be made small. As compared to the semiconductor chip 23 shown in FIG. 6, the left portion of the spacer 68 can be positioned near the light reception portion 61 without degrading the characteristics of the horizontal transfer channel 66a, floating diffusion region 66c and amplifier 67. By considering the adhesive protrusion margin, it is preferable that the adhesion area of the spacer 68 is spaced by, e.g., 50 μm or more, from the upper areas of the floating diffusion region 66c or amplifier 67 (particularly the first stage drive FET 101a or first stage load FET 101b). The solid state imaging unit and semiconductor chip 23 can thus be made compact, particularly along the right/left direction.

As compared to the solid state imaging unit whose photoelectric conversion elements are disposed in the square matrix shape, the solid state imaging unit whose photoelectric conversion elements are disposed in the honeycomb layout has a larger light reception area per pixel, and color data is obtained not only at each pixel position but also at the intermediate positions of adjacent pixels so that a high resolution can be obtained and a more detailed image can be obtained with the same chip size. It is expected that the solid state imaging unit of the honeycomb layout is suitable for use with an endoscope for observing the interior of a living body.

The present invention has been described in connection with the preferred embodiments. The invention is not limited only to the above embodiments. It will be apparent to those skilled in the art that other various modifications, improvements, combinations, and the like can be made.

The solid state imaging unit of the embodiment is suitable for use with various imaging devices which require compactness. The endoscope of the embodiment is suitable as medical endoscopes and the like.

What we claim are:

1. A solid state image pickup device comprising:
   a first area defined on a principal surface of a semiconductor substrate;
   a second area defined on said surface of said substrate and adjacent to said first area; and
   a third area defined on said surface of said substrate and adjacent to said second area, an on a side of said second area which is opposite from said first area,
   wherein said first area includes:
      a plurality of photoelectric conversion elements for accumulating signal charges corresponding to an incidence light amount; and
      a plurality of vertical transfer channels formed adjacent to said plurality of photoelectric conversion elements, said plurality of vertical transfer channels transferring the signal charges read from said plurality of photoelectric conversion elements in a vertical direction toward said second area;
   wherein said second area includes
      a horizontal transfer channel for transferring the signal charges transferred from said vertical transfer channels in a horizontal direction; and
      a first portion of an amplifier, said first portion comprising a floating diffusion region and a first stage drive field effect transistor (FET), and being formed in a horizontal direction from an output port of said horizontal transfer channel; and
   wherein said third area includes a second portion of said amplifier which is formed on an opposite side of said horizontal transfer channel from said first area, and comprises:
      a first state load FET, a second stage drive FET, a second stage load FET, a third stage drive FET and a third stage load FET.

2. The solid state image pickup device according to claim 1, wherein said vertical direction and said horizontal direction cross at a right angle.

3. The solid state image pickup device according to claim 1, further comprising
   a support member adhered to the principal surface of said semiconductor substrate with adhesive and surrounding said first, second and third areas; and
   a transparent member mounted on said support member.

4. The solid state image pickup device according to claim 3, wherein an area where said support member is adhered to the principal surface of said semiconductor substrate, is formed to have an equal width along a longitudinal direction of said support member.

5. The solid state image pickup device according to claim 3, wherein a width of an area where said support member is adhered to the principal surface of said semiconductor substrate, is 100 μm or wider.

6. The solid state image pickup device according to claim 3, wherein a distance from an area where said support member is adhered to the principal surface of said semiconductor substrate to said first stage drive FET or said first stage load FET, is 50 μm or longer.

7. An endoscope comprising:
   a light source for emitting light;
   a solid state image pickup device; and
   a transmission tube accommodating said light source and said solid state image pickup device,
   wherein said solid state image pickup device comprises:
      a first area defined on a principal surface of a semiconductor substrate;
      a second area defined on said surface of said substrate and adjacent to said first area; and
      a third area defined on said surface of said substrate and adjacent to said second area, and on a side of said second area that is opposite from said first area,
   wherein said first area includes:
      a plurality of photoelectric conversion elements for accumulating signal charges corresponding to an incidence light amount; and
      a plurality of vertical transfer channels formed adjacent to said plurality of photoelectric conversion elements, said plurality of vertical transfer channels transferring the signal charges read from said plurality of photoelectric conversion elements in a vertical direction toward said second area;
   wherein said second area includes:
      a horizontal transfer channel for transferring the signal charges transferred from said vertical transfer channels in a horizontal direction; and a first portion of an amplifier, said first portion comprising a floating diffusion region and a first stage drive field effect transistor (FET), and being formed in a horizontal direction from an output port of said horizontal transfer channel; and wherein said third area includes a second portion of said amplifier which is formed on a side of said horizontal transfer channel which is opposite said first area, and comprises:

a first state load FET, a second stage drive FET, a second stage load FET, a third stage drive FET and a third stage load FET.

8. The endoscope according to claim 7, wherein said vertical direction and said horizontal direction cross at a right angle.

9. The endoscope according to claim 7, further comprising:

a support member adhered to the principal surface of said semiconductor substrate with adhesive and surrounding said first, second and third areas; and a transparent member mounted on said support member.

10. The endoscope according to claim 9, wherein an area where said support member is adhered to the principal surface of said semiconductor substrate, is formed to have an equal width along a longitudinal direction of said support member.

11. The endoscope according to claim 9, wherein a width of an area where said support member is adhered to the principal surface of said semiconductor substrate, is 100 μm or wider.

12. The endoscope according to claim 9, wherein a distance from an area where said support member is adhered to the principal surface of said semiconductor substrate to said first stage drive FET or said first stage load FET, is 50 μm or longer.

13. The endoscope according to claim 7, wherein said light source emits white light with light in an infrared range being cut.

14. The endoscope according to claim 7, further comprising a jetting device equipped in said transmission tube, said jetting device jetting out gas or liquid.

15. The endoscope according to claim 7, further comprising a manipulation device equipped in said transmission tube, said manipulation device being capable of holding a target member.

16. The endoscope according to claim 7, further comprising an optical path changing device mounted above said solid state image pickup device, said optical path changing device changing an optical path of incidence light along said first direction and making the light be incident upon said photoelectric conversion elements.

17. The solid state image pickup device according to claim 1, further comprising:

a support member formed on said substrate and having a uniform width, for supporting a protective member.

18. The solid state image pickup device according to claim 17, wherein said support member is formed outside of said first, second and third areas.

19. The solid state image pickup device according to claim 18, wherein said amplifier comprises an outermost portion that is within an innermost portion of said support member.

20. A solid state image pickup device comprising:

a first section formed on a substrate and comprising:

a plurality of photoelectric conversion elements; and a plurality of vertical transfer channels formed adjacent to said plurality of photoelectric conversion elements;

a horizontal transfer channel formed adjacent to said first section and in a vertical direction from said first section;

a floating diffusion region formed adjacent to an output port of said horizontal transfer channel and in a horizontal direction from said output port; and an amplifier comprising:

a first portion formed adjacent to said floating diffusion region and in a horizontal direction from said floating diffusion region; and a second portion formed adjacent to said horizontal transfer channel, and on a side of said horizontal transfer channel that is opposite to said first section.

* * * * *